(12) United States Patent
Chitre et al.

(10) Patent No.: US 8,636,797 B2
(45) Date of Patent: Jan. 28, 2014

(54) INFLATABLE PROSTHESES AND METHODS OF MAKING SAME

(75) Inventors: Kaustubh S. Chitre, Goleta, CA (US); Nicholas J. Manesis, Summerland, CA (US); Nikhil S. Trilokekar, Goleta, CA (US); Dustin Leslie, Santa Barbara, CA (US); David J. Schuessler, Ventura, CA (US)

(73) Assignee: Allergan, Inc., Irvine, CA (US)

( * ) Notice: Subject to any disclaimer, the term of this patent is extended or adjusted under 35 U.S.C. 154(b) by 195 days.

(21) Appl. No.: 13/105,715

(22) Filed: May 11, 2011

(65) Prior Publication Data

US 2011/0270391 A1 Nov. 3, 2011

Related U.S. Application Data

(63) Continuation-in-part of application No. 13/021,523, filed on Feb. 4, 2011.

(60) Provisional application No. 61/301,910, filed on Feb. 5, 2010, provisional application No. 61/409,440, filed on Nov. 2, 2010.

(51) Int. Cl.
*A61F 2/12* (2006.01)

(52) U.S. Cl.
USPC .......................................................... 623/8

(58) Field of Classification Search
CPC ..................................... A61F 2/52; A61F 2/12
USPC .......................................... 623/7–8; 606/192
See application file for complete search history.

(56) References Cited

U.S. PATENT DOCUMENTS

| | | | |
|---|---|---|---|
| 3,577,836 A | 5/1971 | Tamura | |
| 3,919,724 A | 11/1975 | Sanders et al. | |
| 4,157,085 A | 6/1979 | Austad | |
| 4,190,040 A | 2/1980 | Schulte | |
| 4,200,098 A | 4/1980 | Ayer et al. | |
| 4,332,634 A | 6/1982 | Aperavich | |
| 4,428,364 A | 1/1984 | Bartolo | |
| 4,455,691 A * | 6/1984 | Van Aken Redinger et al. . | 623/8 |
| 4,650,487 A | 3/1987 | Chaglassian | |
| 4,662,357 A | 5/1987 | Pierce et al. | |
| 4,685,447 A | 8/1987 | Iversen et al. | |
| 4,840,615 A | 6/1989 | Hancock et al. | |
| 4,889,744 A | 12/1989 | Quaid | |
| 4,908,029 A * | 3/1990 | Bark et al. ........................ | 623/8 |
| 4,969,906 A | 11/1990 | Kronman | |
| 5,005,591 A | 4/1991 | Austad | |

(Continued)

FOREIGN PATENT DOCUMENTS

| | | |
|---|---|---|
| EP | 0324234 | 7/1989 |
| EP | 0412703 | 2/1991 |

(Continued)

*Primary Examiner* — Andrew Iwamaye
(74) *Attorney, Agent, or Firm* — Linda Fox

(57) ABSTRACT

An inflatable tissue expander or more permanent prosthesis, suitable for implantation in a breast, is provided. The tissue expander includes a puncturable, self-sealing anterior portion forming a fillable cavity, and posterior portion that is puncture resistant. The anterior portion includes a silicone-based elastomer material having a mesh embedded therein. The posterior portion includes a first composite guard and a second composite guard, each composite guard including an arrangement of puncture resistant members and a flexible substrate having a first side on which the puncture resistant members are disposed in a spaced apart fashion.

7 Claims, 13 Drawing Sheets

(56) References Cited

U.S. PATENT DOCUMENTS

| | | | |
|---|---|---|---|
| 5,026,394 A | 6/1991 | Baker | |
| 5,066,303 A * | 11/1991 | Bark et al. | 623/8 |
| 5,074,878 A * | 12/1991 | Bark et al. | 623/8 |
| 5,133,753 A * | 7/1992 | Bark et al. | 623/8 |
| 5,141,508 A | 8/1992 | Bark et al. | |
| 5,282,857 A | 2/1994 | Perry et al. | |
| 5,340,352 A | 8/1994 | Nakanishi et al. | |
| 5,425,762 A | 6/1995 | Muller | |
| 5,496,368 A | 3/1996 | Wiese | |
| 5,525,275 A | 6/1996 | Iversen et al. | |
| 5,571,183 A | 11/1996 | Kazem et al. | |
| 5,589,176 A | 12/1996 | Seare, Jr. | |
| 5,632,774 A | 5/1997 | Babiam | |
| 5,964,803 A | 10/1999 | Iversen et al. | |
| 6,022,376 A | 2/2000 | Assell et al. | |
| 6,214,331 B1 | 4/2001 | Vanderhoff et al. | |
| 6,692,528 B2 | 2/2004 | Ward et al. | |
| 6,913,765 B2 | 7/2005 | Li et al. | |
| 6,962,739 B1 | 11/2005 | Kim et al. | |
| 7,018,692 B2 | 3/2006 | Kim et al. | |
| 7,914,578 B2 | 3/2011 | Vardi | |
| 7,976,859 B2 | 7/2011 | Beisang et al. | |
| 8,066,758 B2 | 11/2011 | Bogert et al. | |
| 2001/0052141 A1 | 12/2001 | Andersen | |
| 2002/0106953 A1 | 8/2002 | Kim et al. | |
| 2003/0149481 A1 | 8/2003 | Guest et al. | |
| 2003/0233150 A1 | 12/2003 | Bourne et al. | |
| 2005/0170221 A1 | 8/2005 | Kim et al. | |
| 2007/0059375 A1 | 3/2007 | Bourne et al. | |
| 2007/0196454 A1 | 8/2007 | Stockman et al. | |
| 2008/0027534 A1 | 1/2008 | Edwin et al. | |
| 2008/0063716 A1 | 3/2008 | Moro et al. | |
| 2008/0312739 A1 | 12/2008 | Agerup et al. | |
| 2009/0048684 A1 | 2/2009 | Lesh | |
| 2009/0118756 A1 | 5/2009 | Valencon et al. | |
| 2009/0118829 A1* | 5/2009 | Powell et al. | 623/8 |
| 2009/0326654 A1* | 12/2009 | Powell | 623/8 |
| 2010/0049316 A1 | 2/2010 | Schuessler | |
| 2011/0270391 A1 | 11/2011 | Chitre et al. | |
| 2012/0123537 A1 | 5/2012 | Manesis et al. | |
| 2013/0052142 A1 | 2/2013 | Harder et al. | |

FOREIGN PATENT DOCUMENTS

| | | |
|---|---|---|
| EP | 0422302 | 4/1991 |
| EP | 0784987 | 7/1997 |
| GB | 2392077 | 2/2004 |
| WO | 9220519 | 11/1992 |
| WO | 0210667 | 2/2002 |
| WO | 03057462 | 7/2003 |
| WO | 03059617 | 7/2003 |
| WO | 2004021935 | 3/2004 |
| WO | 2008016983 | 2/2008 |
| WO | 2009061672 | 5/2009 |

* cited by examiner

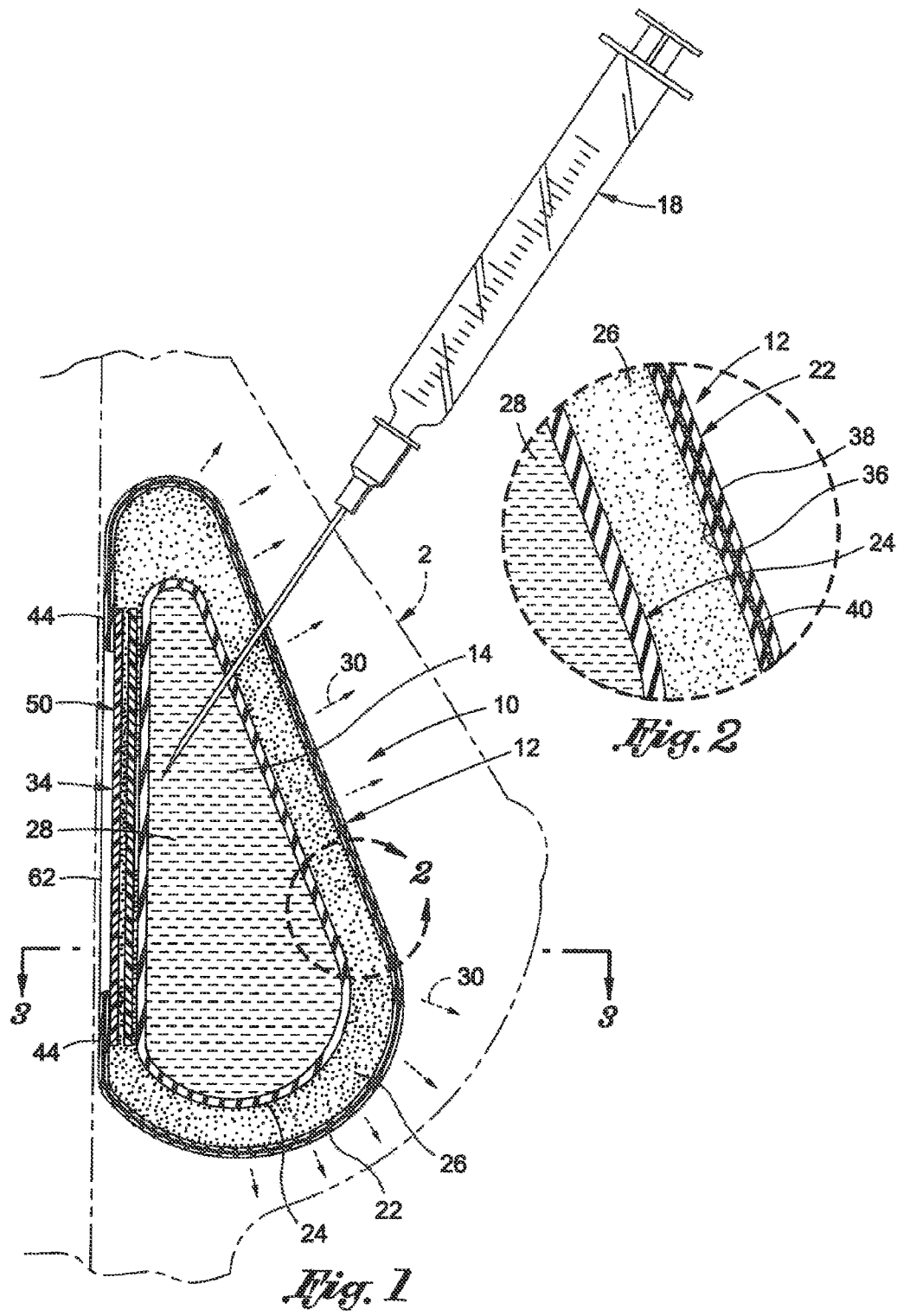

INFLATABLE PROSTHESES AND METHODS OF MAKING SAME

RELATED APPLICATIONS

This application is a continuation-in-part of U.S. patent application Ser. No. 13/021,523, filed on Feb. 4, 2011, which claims the benefit of U.S. Provisional Patent Application No. 61/301,910, filed on Feb. 5, 2010, and the benefit of U.S. Provisional Patent Application No. 61/409,440, filed on Nov. 2, 2010, the entire disclosure of each of these applications being incorporated herein in its entirely by this reference.

BACKGROUND INFORMATION

The present invention generally relates to medical implants and more specifically relates to inflatable prostheses, such as tissue expanders, suitable for implantation in a mammal.

Prostheses or implants for reconstruction and/or augmentation of the human body are well known.

Fluid filled prostheses, for example, mammary prostheses or breast implants, are widely used to replace excised tissue, for example after a radical mastectomy, or to augment the body to improve surface configurations. Although there are many applications where these are used, the most common is the mammary prosthesis, used to augment or otherwise change the size or shape of the female breast.

A conventional saline-filled breast implant includes an outer shell of several layers of silicone elastomer having a valve or fill port. The prosthesis is typically implanted into the breast cavity in an empty or only partially filled state. The implant is then inflated to its final size by means of the valve or fill port. This helps reduce the size of the needed incision, and enables a surgeon to adjust and even microadjust the volume of the implant. Unfortunately, the valve or fill port is sometimes noticeable to the touch.

Many or even most implants are manufactured to a given size and shape, and are implanted without means or expectation of changing their size after implantation or initial filling when first inserted into the breast. However, in many situations it is desirable to be able to adjust the size of the implant over a substantial period of time. If the volume can later be adjusted, an implant of lesser initial volume can be implanted, and as the post-surgical swelling goes down, the implant used as a prosthesis can be enlarged. Also, because often the procedure is for cosmetic purposes, it is useful to be able to make a later adjustment of size without having to replace the prosthesis with one of a different size, which would require a subsequent surgical procedure.

One problem with many conventional adjustable implants is that they require a valve to be part of the implant.

It would be advantageous to provide an adjustable volume implant which does not require a valve or other access port for receiving fluid for adjustment.

Prior to implantation of a more permanent prosthesis, it is common practice to utilize a more temporary implant, for example, what is known as a "tissue expander" in order to gradually create the space necessary for the more permanent prosthesis. Keeping living tissues under tension by means of a tissue expander causes new cells to form and the amount of tissue to increase. Conventionally, a tissue expander comprises an inflatable body, having an inflation valve connected thereto. The valve may be formed into the inflatable body itself or may be remotely located and connected to the inflatable body by means of an elongated conduit.

The inflatable body of the tissue expander is placed subcutaneously in the patient, at the location of where tissue is to be expanded. The inflation valve, whether on the implant or remote thereto, is also subcutaneously positioned or implanted, and is configured to allow gradual introduction of fluid, typically saline, into the inflation body, by injection with a syringe. After gradual inflation at pre-determined intervals, the skin and subcutaneous tissues overlying the expander are consequently caused to expand in response to the pressure exerted upon such tissues by the inflatable body as solution is gradually introduced therein.

After gradual inflation at pre-determined intervals, which may extend over weeks or months, the skin and subcutaneous tissue will expand to the point where further medical procedures can be performed, such as the permanent implantation of a prosthesis, plastic and reconstructive surgery, or for use of the skin and subcutaneous tissue for use in some other part of the body.

During a mastectomy, a surgeon often removes skin as well as breast tissue, leaving the remaining chest tissues flat and tight. To create a breast-shaped space for a reconstructive implant, a tissue expander is sometimes used as described above.

In any event, it should be appreciated that locating the fill valve on a prosthesis such as a tissue expander or adjustable implant requires considerable practitioner skill. Attempts to make products which facilitate this include the development of various products having structure, for example, embedded magnets or a raised ring, for assisting physicians in locating the valve.

It has also proven difficult to develop a flexible protective material that is effective as a puncture resistant material while also being safe for implantation in the body. A puncture resistant material used as a component of a breast implant or tissue expander would ideally be sufficiently flexible such that the implant could still be folded or rolled and inserted through a small incision while also providing resistance to needle punctures aimed at inflating the implant/expander to its final size.

Bark et al., U.S. Pat. No. 5,066,303 discloses a self-sealing tissue expander with a shell having a flowable sealing material. According to Bark et al., fluid infusion into the shell can be done directly through the shell, without the need for a fluid entry port.

Schuessler, U.S. patent application Ser. No. 12/543,795, filed on Aug. 19, 2009, the entire disclosure of which is incorporated herein by this specific reference, discloses a fluid filled implant including a self-sealing shell.

There is a need for improved temporary tissue expanders, more permanent adjustable implants, and other inflatable prostheses. The present invention addressed this need.

SUMMARY OF THE INVENTION

The invention relates to expandable prostheses, for example, implants and tissue expanders, and in particularly to implantable temporary tissue expanders as well as more permanent mammary prostheses.

Accordingly, the present invention provides implants, for example but not limited to tissue expanders and more permanent prostheses, for example, those implantable in a breast, and methods of making same. The present invention provides inflatable prosthetic implants, components thereof and methods of making same. In one aspect of the invention, inflatable prosthetic implants are provided which include, as a component of such implants, flexible, puncture resistant materials.

In another broad aspect of the invention, inflatable implants or prostheses, for example, tissue expanders and adjustable implants are provided which generally comprise a puncturable, self-sealing anterior portion, or shell, a puncture resistant posterior portion substantially opposing the anterior portion, and a fillable cavity defined between the anterior portion and the posterior portion.

It is to be appreciated that the terms "implant" "prosthesis" and "tissue expander" as used herein are intended to encompass permanent implants, including adjustable implants, as well as relatively temporary tissue expanders, and components, for example, shells, of such implantable devices.

In one aspect of the invention, a method of making an inflatable device or prosthesis, suitable for implantation in a mammal, is provided wherein the method generally comprises the steps of providing a plurality of mesh segments, positioning the plurality of segments on a curved molding surface, applying a fluid elastomeric material to the molding surface with the segments positioned thereon, and allowing the elastomeric material to set to form a flexible shell having an open end, the shell including the fabric segments embedded within the set elastomer, and the shell being useful as a component of an inflatable prosthesis. The step of positioning may substantially entirely covering the molding surface with the mesh segments, for example, in a manner such that the mesh segments overlap one another. The method further comprises the step of sealing the open end of the elastomeric shell, for example, by providing a puncture resistant member and sealing the puncture resistant member to the open end of the elastomeric shell.

In one embodiment, the mesh segments comprise a non-stretchable mesh fabric, for example, a substantially non-expanding polyester fabric mesh. In another embodiment, the mesh segments comprise a stretchable mesh fabric.

The method may further comprise the step of applying a tacky material to the curved molding surface prior to the step of positioning the mesh. The tacky material may be a fluid elastomeric material, for example, a silicone dispersion.

In another embodiment, the method comprises pre-shaping, for example, thermoforming, a mesh element, from a two-dimensional sheet into a three dimensional "sock" having the general shape of the molding surface. The method includes positioning the pre-shaped mesh element onto the molding surface, applying a fluid elastomeric material to the molding surface with the pre-formed mesh positioned thereon, and allowing the elastomeric material to set to form a flexible shell having an open end, the shell including the preformed mesh embedded within the set elastomer, and the shell being useful as a component of an inflatable prosthesis.

In another aspect of the invention, an inflatable prosthesis made by the methods described herein is provided.

Further, in another aspect, an inflatable prosthesis in accordance the invention generally comprises an interior shell defining an inflatable chamber, an exterior shell comprising a silicone-based elastomer material having a mesh embedded therein, a gel separating the interior shell and the exterior shell, and a puncture resistant member forming a base of the prosthesis.

In yet another aspect of the invention, a method of making a needle guard for an inflatable prosthesis suitable for implantation in a mammal is provided. The method generally comprises the steps of providing a first layer of puncture resistant members, for example, elongated slates, providing a second layer of puncture resistant members such that the second layer of members overlies and is offset from the first layer of members, molding or otherwise applying a flexible material to the first layer of members and the second layer of slats to form a device useful as a needle guard for an inflatable prosthesis. The step of applying or molding includes coupling the members to, for example, encasing the members within, the flexible material.

In one embodiment, the members are elongated slats, and the slats of the first layer are substantially parallel to the slats of the second layer. The slats may be made of any suitable puncture resistant material, for example, a material selected from the group of materials consisting of acetal, nylon, and polycarbonate. In some embodiments, the slats are made of a metal, for example, stainless steel, aluminum or titanium. The slats may be individual, separate elements that are cut from a sheet of material using any suitable means such as laser cutting. In other embodiments, at least one of the first layer of slats and the second layer of slats comprises a single sheet, undivided sheet of material having grooves defining the adjacent slats.

In some embodiments, the step of applying a flexible material comprises applying an elastomeric sheet between the first layer of slats and the second layer of slats, for example, applying an uncured elastomeric sheet between the first layer of slats and the second layer of slats, and subsequently curing the sheets.

Alternative to the first and second layers of slats, it is contemplated that a puncture-resistant fabric may be used, for example, in conjunction with an elastomeric layer, to form a suitable needle guard.

In one aspect of the invention, a method for making an inflatable prosthesis suitable for implantation in a mammal is provided, wherein the method comprises providing a needle guard made by a method of the invention as described elsewhere herein and securing a flexible, inflatable shell to the needle guard.

In another aspect of the invention, an inflatable prosthesis is provided generally comprising a flexible shell forming an anterior surface of the prosthesis, wherein the needle guard forms at least a portion of a posterior surface of the prosthesis, and comprises a elastomer portion and a first layer of puncture resistant slats embedded in the elastomer portion. The needle guard may further comprise a second layer of puncture resistant slats. In some embodiments, the second layer of slats is offset from the first layer of slats.

In yet another aspect of the invention, flexible, resilient puncture resistant assemblies are provided, the assemblies being, useful as components of surgical implants, for example, but not limited to, needle guards as components of inflatable implants that are accessed with a needle and syringe. Such implants for which the present materials are useful include inflatable tissue expanders. Other implants that can benefit from the present invention include fluid access ports which include a fluid reservoir and needle penetratable septum. In these and other implantable devices, puncture resistant or puncture proof assemblies of the invention can be highly beneficial, for example, as a means for preventing a needle tip from penetrating other areas of the device that are not intended to be punctured. Other beneficial uses for the present assemblies will become more apparent upon reading the present specification, and are considered to be included within the scope of the invention.

For example, puncture resistant assemblies are provided which are flexible and/or formable into desired configurations.

In some embodiments, puncture resistant assemblies are provided which are both flexible and resilient. Some of the present assemblies have the characteristic of shape memory, such that after being rolled or folded, they can resume an original shape or configuration. This aspect of the invention is particularly, but certainly not exclusively, useful for application in a surgical environment, in which the assembly may be in the form of a puncture proof material is rolled or folded into a narrow configuration, thereby enabling insertion thereof through a relatively small incision. Advantageously, some of the assemblies of the invention are structured to be able to automatically resume an original, pre-deformed shape, for example, automatically, once the material is at the desired implantation site.

In one embodiment of the invention, a puncture resistant assembly is provided which generally comprises a first composite guard, a second composite guard, and a intermediate layer securing the first and second composite guards together and/or containing the first and second composite guards.

Each of the first and second composite guards generally comprises an arrangement of puncture resistant elements or members, and a flexible substrate on which the members are secured and positioned, generally in a spaced-apart relationship.

The members may be in the form of domes or plates. The members have a hardness effective to resist penetration, puncture or breakage upon forceful contact with a sharp surface, for example, a tip of a needle, an edge of a cutting implement such as a scalpel or knife, or the like. The members may be made of any suitable material, such as a hard moldable substance, for example, a high durometer elastomer, polymer or rubber. Other suitable materials include metals, ceramics, and alloys thereof.

The flexible substrate on which the members are disposed may comprise a fabric, mesh, film, elastomer, or other material.

Notably, the first composite guard and the second composite guard are disposed with respect to one another such that the arrangement of members of the first composite guard is offset or misaligned with respect to the arrangement of members of the second composite guard. In some embodiments, a third composite guard is provided. The third composite guard may be positioned with respect to the first and second composite guards such that the members of the third composite guard are misaligned with the members of at least one of the first and second composite guards.

Advantageously, the misaligned or overlapping members of the adjacent composite guards provide a puncture resistant, or puncture proof, area while not significantly sacrificing flexibility of the assembly as a whole. That is, the composite guards may be arranged such that there are no significant gaps between individual puncture resistant members. It can be appreciated that depending upon the use of the final assembly, there may be some gaps between members so long as the gaps are sufficiently narrow to resist or prevent penetration by the type of instrument that the assembly is intended to be protected against puncture from.

In any event, in some embodiments of the invention, the puncture resistant members of the composite guards may provide a area of protection that substantially entirely covers a first side of the needle guard assembly.

The assembly may further comprise a intermediate layer, for example, an elastomer, securing together the first and second composite guards such that the members maintain their offset relationship. The intermediate layer may be located between adjacent composite guards and may be bonded thereto. In one embodiment, the intermediate layer seals the flexible composite members together and encapsulates the composite guards. For example, the intermediate layer may be an fluid tight barrier containing the two or more layered composite guards. In some embodiments, the intermediate layer exhibits a springiness and resiliency or provides a shape memory characteristic to the assembly.

In another aspect of the invention, a method of making a needle guard assembly is provided wherein the method generally comprises the steps of providing first and second composite guards where each composite guard includes a layer of puncture resistant members secured to a flexible substrate and bonding the first composite guard with the second composite guard in such that the members of the first composite guard are misaligned with the members of the second composite guard. In some embodiments, the method includes the step of bonding a third composite guard to the second composite guard such that the members of the third composite guard are misaligned with the members of at least one of the first composite guard and the second composite guard.

In some embodiments, the method may comprise the step of providing an intermediate layer between the composite guards. In some embodiments, the method may comprise the step of encasing or encapsulating the composite guards in a fluid tight seal.

In one embodiment, an inflatable prosthesis is provided which comprises an inflatable portion including an interior shell, an exterior shell comprising a silicone-based elastomer material having a mesh embedded therein and a gel separating the interior shell and the exterior shell. The prosthesis further comprises a needle guard assembly comprising a first composite guard and a second composite guard, each composite guard including an arrangement of puncture resistant members and a flexible substrate having a first side on which the puncture resistant members are disposed in a spaced apart fashion. The first composite guard and the second composite guard are positioned such that the arrangement of puncture resistant members of the second composite guard are misaligned with the arrangement of puncture resistant members of the first composite guard. The needle guard assembly further comprises an intermediate layer disposed between and connecting the first composite guard with the second composite guard.

In one aspect of the invention, the shell of the prosthesis comprises a self-sealing laminate defining an interior chamber of the prosthesis. The laminate generally includes a base layer formed from an elastomer, a layer of silicone of sufficient thickness for self-sealing of a needle hole therethrough and a top layer formed from an elastomer. The laminate may have a total thickness for enabling an internal chamber pressure of about 2.5 psi within an expander exterior compressor force of about 40 lbs.

More specifically, the laminate in accordance with this embodiment includes base and top layers formed from one type of silicone elastomer and an intermediate layer disposed between the base and top layers, formed of another type of silicone elastomer. For example, the base and top layers may be formed of Nusil PN-3606-1 and the intermediate layer may be formed of Nusil MED-6350.

In an exemplary embodiment, the base layer has a thickness of about 0.006 inches, the top layer has a thickness of about 0.006 inches, and the intermediate layer has a thickness of between about 0.100 inches and 0.120 inches.

An additional layer, for example, a polyester mesh layer, may also be provided as a part of the laminate to insure integrity of the tissue expander.

Each and every feature described herein, and each and every combination of two or more of such features, is included within the scope of the present invention provided that the features included in such a combination are not mutually inconsistent.

BRIEF DESCRIPTION OF THE DRAWINGS

The present invention may be more clearly understood and certain aspects and advantages thereof better appreciated with reference to the following Detailed Description when considered with the accompanying Drawings of which:

FIG. 1 is cross-sectional view of a tissue expander in accordance with an embodiment of the invention, the tissue expander shown as implanted in a breast of a human being;

FIG. 2 is magnified view of a portion of the expander shown in FIG. 1;

DETAILED DESCRIPTION

Figure 3:
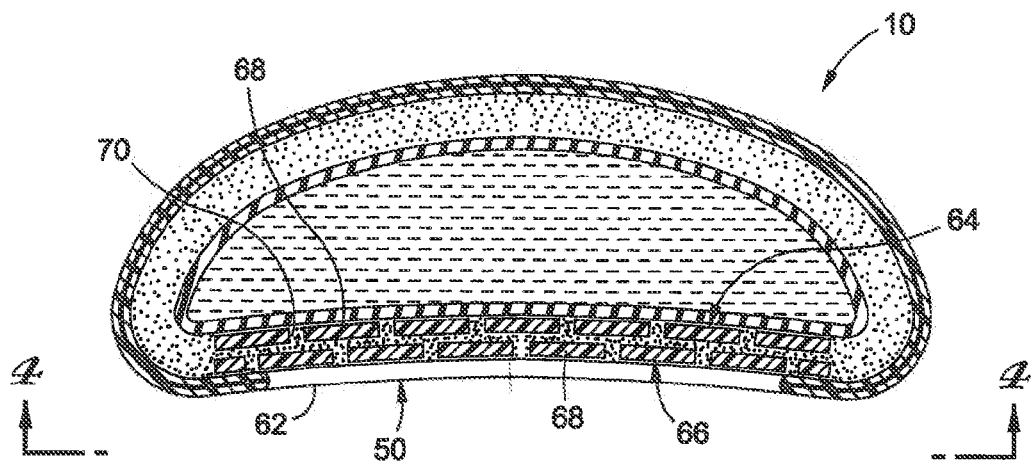
FIG. 3 is a cross-sectional view of another tissue expander in accordance with the invention.

The present invention generally pertains to implantable inflatable devices and methods for making same, for example, devices such as soft fluid-filled implants, for example, but not limited to, permanent or temporary implants useful in breast reconstruction or breast augmentation procedures.

Turning now to FIG. 1, an inflatable device, in accordance with one embodiment of the invention, is shown generally at 10, as implanted in a human breast 2. The device 10 is being inflated with a suitable fluid, such as a saline solution 14, by means of a typical syringe 18.

The device 10 generally comprises an inflatable portion 12 comprising outer shell 22, an inner shell 24 and a intermediate layer 26 therebetween. The inner shell 24 defines an inflatable cavity 28 (shown here as being filled with saline solution 14).

Inflation of the cavity 28 causes expansion of the device as shown by arrows 30. The device 10 further includes a posterior portion 34 that is generally resistant to expansion upon inflation of cavity 28. The total volume of the device 10 is adjustable by introduction and removal of fluid into and from the fillable cavity 28.

The outer shell 22 of the device 10 may comprise at least one layer of elastomeric material, for example, a first layer 36 of elastomeric material and a second layer 38 of elastomeric material, and an additional layer of a different material, for example a reinforcement layer 40, located between the first and second layers 36, 38 of elastomeric material.

The elastomeric material may be a silicone elastomer such as a dimethyl silicone elastomer, for example, a substantially homogeneous dimethyl-diphenyl silicone elastomer. One composition useful in the present invention is described in Schuessler, et al., U.S. application Ser. No. 12/179,340, filed Jul. 24, 2008, the disclosure of which is incorporated herein in its entirety by this specific reference. The elastomeric material may comprise a room temperature vulcanizing (RTV) or a high temperature vulcanizing (HTV) silicone from about 0.1-95 wt %, for example, about 1-40 wt %, for example, about 30 wt %. In an exemplary embodiment, the silicone-based fluid material is a high temperature vulcanizing (HTV) platinum-cured silicone dispersion in xylene.

The reinforcement layer 40 may comprise a mesh or fabric, for example, a synthetic polymer mesh or fabric, for example, a mesh or fabric made from polyethylene terephthalate) (PET), polypropylene (PP), polyurethane (PU), polyamide (Nylon), polyethylene (PE), any other suitable material, or combinations thereof.

In an exemplary embodiment, the outer shell 22 is made by dipping two or more layers of silicone-based elastomer over a conventional breast implant mandrel, followed by placement of a pre-fabricated 2 or 4-way stretchable "sock" of the said reinforcing material layer 40, followed by two or more dips of the silicone-based elastomer. The reinforcing "sock" is able to take the shape of the mandrel and the fabric is trapped on both sides between the elastomer layers 36, 38. In this embodiment, the stretchable pre-shaped "sock" (which may form the reinforcing layer 40 of outer shell 22) can be relatively easily mounted on the mandrel because of its flexibility and elasticity, making it easier to manufacture a reinforced shell with the intended shape and dimensions of the mandrel. The entire assembly forming the outer shell 22 is heated in an oven at a temperature and time suitable to cure the silicone.

Figures 8, 9:
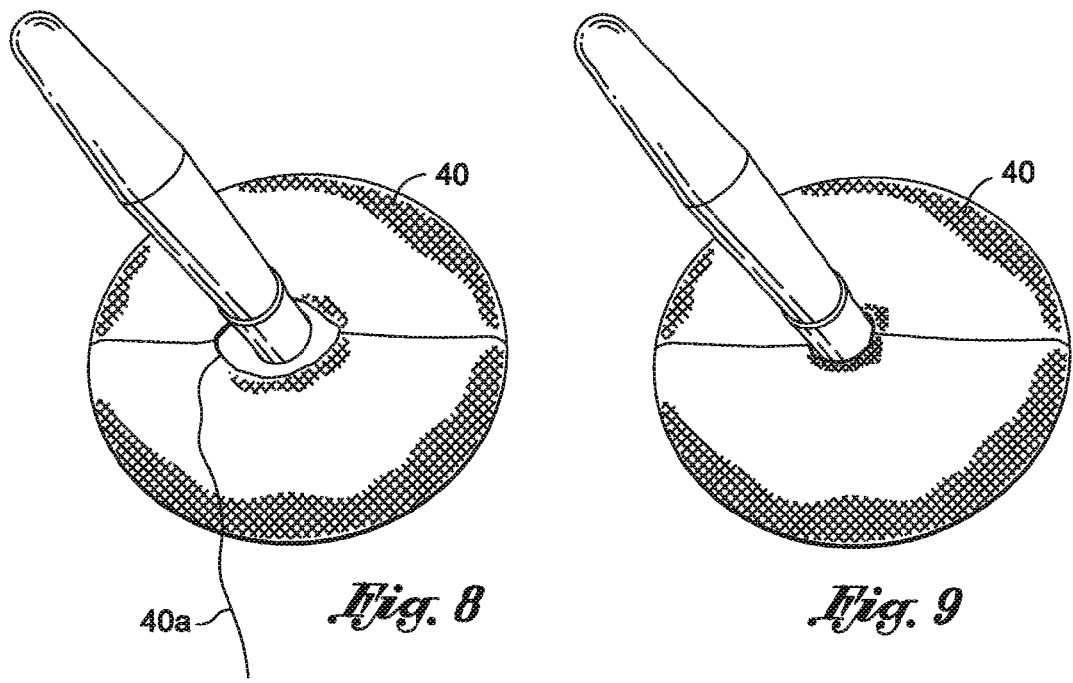
FIGS. 8-10 show steps useful in making some of the tissue expanders of the present invention.
Figure 10:
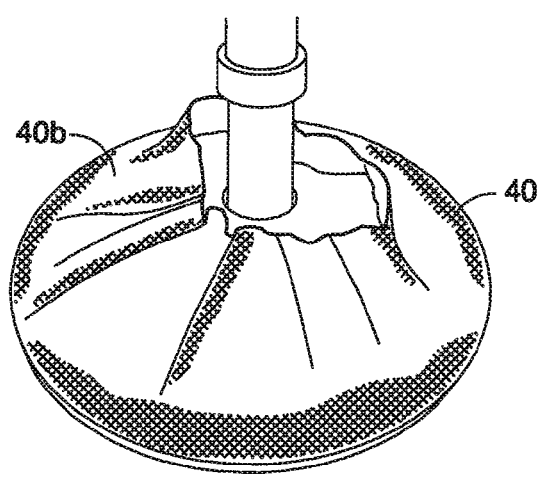

In one embodiment of the invention, the reinforcement layer 40 is provided by forming a "sock" by using a cinch 40a as illustrated in FIGS. 8 and 9. Alternatively, the reinforcement layer 40 is thermoformed into "sock" by placing a single sheet of suitable material, for example a non-stretchable mesh, over a a curved molding surface, for example, a mandrel, and gathering the mesh material at 40b, as shown in FIG. 10. The gathered mesh material is shaped, for example, thermoformed, to take on the 3-D shape of the mandrel.

Alternatively, rather than mesh sock, the reinforcement layer may comprise a plurality of fabric or mesh segments which are positioned on a mandrel or other curved molding surface. The segments may substantially entirely cover the molding surface. The segments may be positioned such that they overlap one another. The molding surface may first be contacted with a tacky material, for example, contacted with or coated with a silicone elastomer dispersion, to facilitate adherence of the segments thereto. An elastomeric material, such as an uncured silicone sheet or a silicone dispersion is applied to the molding surface with the segments positioned thereon. The elastomeric material is allowed to set to form a flexible shell having an open end, the shell including the fabric or mesh segments embedded within the set elastomer, and the shell being useful as a component of an inflatable prosthesis.

Post-curing, the reinforced shell is removed from the mandrel, and another elastomeric shell (which forms the inner shell 24) is placed inside the first shell (which forms the outer shell 22). The inner shell 24 may be a typical unreinforced elastomeric shell, or alternatively may be made similarly to that described above with respect to the outer shell 22. The inner shell 24 may have the same or smaller size relative to outer shell 22. The two shells 22, 24 are vulcanized close to their open base using, for example, a ring-shaped patch 44, thus forming an inter-shell compartment. The dual-shell assembly is mounted back on a mandrel. The size of the mandrel can be the same as the one used for the inner shell fabrication or slightly larger. The latter would result in a laterally stressed inner shell with potentially enhanced sealing properties.

In some embodiments of the invention, at least one of the inner shell 24 and the outer shell 22 comprises an elastomeric material comprising a substantially homogenous layer of a silicone elastomer comprising a polysiloxane backbone and having a minimum mole percent of at least 10% of a substituted or pendant chemical group that sterically retards permeation of said silicone gel through the layer. More specifically, in this embodiment, the silicone elastomer is a polydimethyl siloxane and the pendant chemical group is one of a phenyl group, for example, a diphenyl group or a methylphenyl group, a trifluoropropyl group, and mixtures thereof. Such materials are described in detail in Schuessler, et al., U.S. patent application Ser. No. 12/179,340, filed on Jul. 24, 2008, the entire disclosure of which is incorporated herein by this specific reference. This material may make up one or more layers of the shell(s) 22, 24.

After the inner shell 24 and outer shell 22 are bonded together, a cavity formed therebetween is then filled with a material, for example, a flowable material, for example, a silicone gel. This may be accomplished using any suitable means known to those of skill in the art. In one embodiment, the gel is introduced through a reinforced silicone plug on the outer shell 22. The silicone gel between the outer and inner shells 22, 24, forms the intermediate layer 26. After filling, the assembly made up of the inner shell 24, outer shell 22 and intermediate layer 26, is cured, for example, by exposing the assembly to heat in an oven for a suitable length of time. The mandrel that defines the desired shape of the implant can be round or oval, with a lower or upper pole for optimal projection. Before sealing the implant with a patch, a needle guard element, such as that described and shown elsewhere herein, may be inserted and bonded to the inner shell 22 and/or outer shell 24, to form the posterior portion 34 of the device.

It can be appreciated that the device 10, in the form of a tissue expander, once implanted in a patient, must be repeatedly accessed during the expansion process with percutaneous needle punctures, such as shown in FIG. 1. In some embodiments, the tissue expander devices are able to survive repeated puncturing and over-expansion to 200% by saline without leakage.

The device 10 can also be in the form of a more permanent mammary prosthesis, for example an adjustable breast implant. The volume of the implant can be adjusted in situ by accessing the cavity 28 with a needle through the self-sealing anterior portion of the device 10. In some embodiments, the cavity 28 has a small volume relative to the gel portion 26, to provide a comfortable implant having the desirable qualities of a gel-filled implant with the advantages of being size-adjustable with saline.

In summary, the anterior surface of the device 10 is self-sealing and can be accessed for fluid communication. The mechanism of self-sealing is facilitated by a combination of the gel layer 26 and shell 22. After a void is created by a needle used to introduce filler (saline) into the implant 10, the gel layer 26 prevents the saline 14 from having a direct path to the exterior and the reinforcing mesh 40 enhances this property by physically constraining the gel from expansion under pressure exerted by the saline 14. The reinforcing materials 40 include but are not limited to meshes and fabrics made from PET, PP, PU, Nylon, etc. and combinations thereof. This invention features a novel manufacturing method for shaping the implant shell into 2-D and 3-D structures making it more convenient to manufacture and convert these reinforced structures into mammary prostheses.

In order to limit the depth of penetration of the needle, and also to give the medical professional feedback as to when the needle has reached the correct location for filling, conventional (prior art) tissue expander devices sometimes include a rigid backing or needle stop behind the filling port in the posterior side of the device. Typically these needle stops are made of metals or very hard or thick plastics to prevent needle penetration through the injection site. By nature then, these needle stops are quite rigid and inflexible, can be uncomfortable, and can limit the collapsibility of the device which affects ease of insertion of the expander through the initial incision.

In one aspect of the present invention, the posterior portion 34 of device 10 may comprise an improved needle guard 50. The needle guard 50 may comprise any suitable biocompatible polymer (e.g. PE, PP, PU, PET, PI, TPU, high durometer silicones, ABS etc.) that is strong enough to resist needle puncture. The needle guard 50 may comprise one or more layers 56 of puncture resistant material with or without an intermediate layer 58. In some embodiments, the needle guard 50 is structured so as to prevent, or substantially prevent, the device 10 from expanding toward the chest wall during inflation of cavity 28.

For filling an implant of the present invention, syringe coupled to a 21 g or smaller needle may be used. The needle may be introduced anywhere in the anterior portion of the implant, such that it reaches the needle guard 50, where it is prevented from penetrating further. The implant is then filled with saline or other liquids for tissue expansion. After removal of the needle, the assembly (e.g. outer shell 22, inner shell 24 and intermediate layer 24) self-seals and prevents the implant from leaking.

Figure 4:
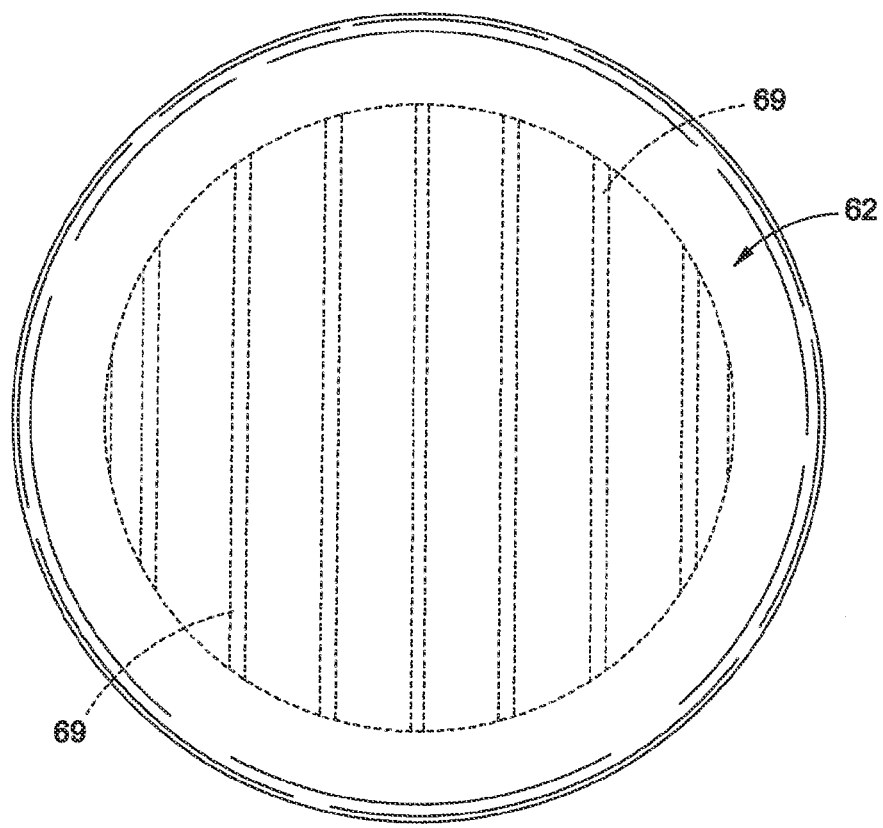
FIG. 4 is a cross-sectional view taken along line 4-4 of FIG. 3.

In FIGS. 3 and 4, the needle guard 50 may comprise an elastomer portion 62, and one or more layers of puncture resistant members coupled thereto. In the shown embodiment, members comprise elongated members, for example, slats 68 coupled to the elastomer portion 62.

In this case, the needle guard 50 comprises one or more layers of slats 68, for example, a first layer 64 of slats 68 and a second layer 66 of slats 68 coupled to the elastomer portion 62. As shown, the slats 68 of the first layer 64 overlap, or are offset from, the slats 68 of the second layer 66. For example, spacing between slats 68 of the first layer 64 are aligned with slats of the second layer and vice versa. Elastomer portion 62 may include grooves 69 or slots. Grooves may be aligned with slats 68 to facilitate rolling or folding of the device 10.

Slats 68 extend across substantially the entire posterior portion 34 and are aligned substantially parallel to one another. This arrangement allows the device 10 to be rolled or folded in alignment with the slats 68 while the offset or overlapping positioning of the first and second layers 64, 66 provides protection in the event a needle enters spacing 70 between adjacent slats 68.

Alternative to this arrangement, adjacent slats in each layer may overlap one another (not shown). The needle guard comprises overlapping but independent small pieces of rigid puncture-resistant material, and like the offset layers of slats 68 described and shown elsewhere herein, the overlapping configuration provide that there are no "line-of-sight" openings through which a needle can pass.

Slats 68 may be a polymer material. Slats may be, for example, nylon, acetal, polycarbonate, or other suitable, biocompatible, puncture resistant or puncture-proof polymeric material. Slats 68 may be metal, for example, stainless steel, aluminum or titanium.

In various exemplary embodiments, slats 68 may be between about 10 mm to about 100 mm or more in length, about 2 mm to about 30 mm in width, and about 0.2 mm to about 4 mm in thickness. Slats of other configurations and dimensions suitable for achieving the desired flexibility of the needle guard 50 may also be used. Such variations of materials and dimensions are considered to fall within the scope of the present invention. In one embodiment, slats 68 have a thickness of about 2 mm and the needle guard 50, including first and second layers 64, 66 of slats 68 and elastomer material therebetween, has a total thickness of 5.0 mm or less.

Slats 68 may be formed by laser cutting same from a sheet of material. Alternatively, slats 68 may be defined by grooves in a single sheet of material. In this specific example, the 2 layers of parallel slats of puncture-resistant plastic about 0.25" wide and with about 0.05" open space between each slat. The layers are offset from each other so that the open space of one slat layer is centered on the middle of a slat in the layer below. All the slats are encapsulated in a soft flexible material like silicone. The open space between the slats gives the whole assembly flexibility to be readily folded or rolled up even though the plastic itself is rigid and resistant to extensive bending. Other shapes and layering designs of independent pieces of puncture resistant materials would provide the needle stop with more and different degrees of bending and folding capability.

The rigid or semi-rigid material forming the slats could be thermoplastics such as acetal, nylon, polycarbonate, and others; or thin metals such as stainless steels, aluminum, or titanium. The use of plastics can be advantageous in that the entire device 10 can be made to be MRI compatible.

In a similar aspect of the invention, thin elastomeric films (0.25 mm-1 mm) made of materials resistant to needle puncture may be used as a component of the needle guard portion of the implant. In some embodiments, such films can be provided with grooves in their design to allow folding/unfolding during insertion. The films may be attached to the shell using adhesives or alternatively may be are encapsulated in silicone.

In another embodiment, rather than independent slats 68, one or more layers of flexible "slat sheets" are provided. In this embodiment, adjoining slats could be made by starting with readily available sheets of the desired plastic of the appropriate thickness. Parallel, adjacent slats are created by laser cutting through the plastic to create the desired spacing between slats but not all the way to the edges of the plastic sheet, thereby leaving a material, for example, a border that holds all the slats together. In this way the pre-cut slats can still be handled as one piece and therefore maintain the desired spacing and orientation. In one embodiment, two of these pre-cut plastic "slat sheets" are alternately layered between 3 sheets of silicone. After curing the silicone, a die cutter of the desired shape of the needle stop can cut within the borders of the pre-cut slats to stamp out the finished needle stop that now has many unconnected slats each independently encased in silicone.

Alternatively still, the pre-cut slat sheets could be held in the desired orientation in a mold and silicone could be injected and cured around them. Additional assembly steps could include creating a silicone border around the needle stop that would assemble to the expander envelope, texturing or adding features to the needle stop surface, or shaping the needle stop assembly so that it has a concave exterior to better fit the chest wall anatomy in the case of a breast tissue expander.

Figure 4A:
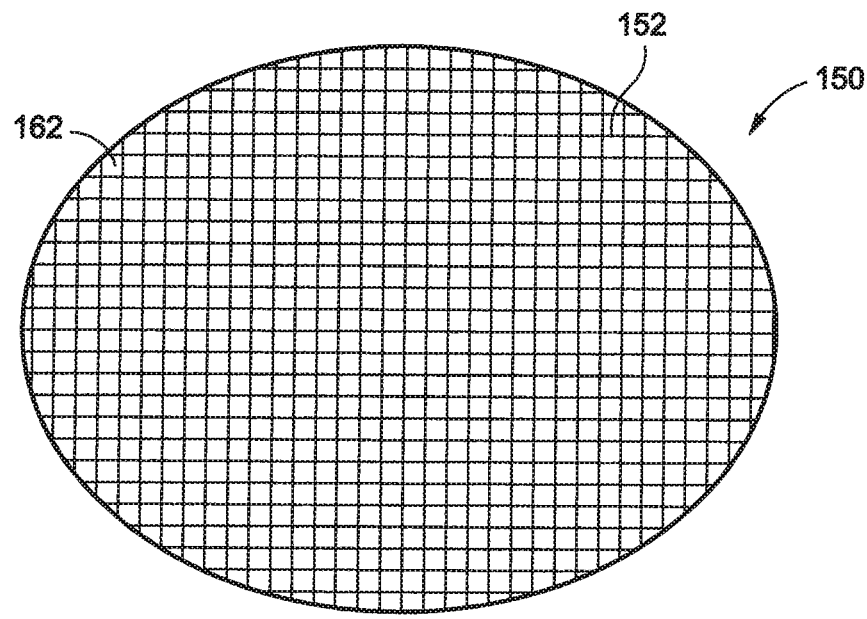
FIGS. 4A and 4B are a simplified top view and cross sectional view, respectively, of a needle guard feature of the tissue expanders of the present invention.
Figure 4B:
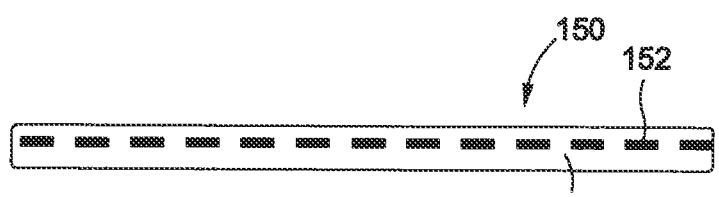

Turning to FIGS. 4A and 4B, yet another variation of a needle guard 250 is provided, similar to needle guard 50, except that rather than slats 68, one or more layers of a puncture resistant mesh 152 are provided. Needle guard 150 may be substantially identical to needle guard 50 described above, with one or more differences being as follows.

In the shown exemplary embodiment, the needle guard 150 comprises one or more layers of mesh 152, for example, a single layer of mesh 152 coupled to, for example embedded in, the elastomer portion 162. In other embodiments, not shown, two or more layers of mesh are provided, wherein fibers or cords making up the mesh, in adjacent layers of mesh, overlap one another. For example, interstices or spacing between mesh fiber of a first layer of mesh aligns with the mesh fiber of a second layer of mesh, and vice versa. Alternatively, a single layer of mesh is provided with interstices between fibers being sized to prevent needle penetration therethrough.

Flexibility of mesh 152 and elastomer portion 162 allow the entire implant device to be rolled or folded upon insertion into a breast cavity through a small incision.

Mesh 152 may be a polymer or a metallic material. Mesh may be, for example, a polymer such as nylon, acetal, polycarbonate, or other suitable, biocompatible, puncture resistant or puncture-proof material. Mesh 152 may be metal, for example, stainless steel, aluminum or titanium.

It should be appreciated that in many of the embodiments of the present invention, the needle guard making up the posterior portion of the implant comprises puncture resistant members arranged in an overlapping configuration to provide no "line-of-sight" openings through which a needle can pass. These puncture resistant members can be variously configured and arranged to achieve this goal.

In a preferred embodiment, it is desirable for the needle stop to be flexible for insertion yet rigid to resist needle puncture. To prevent movement of the needle guard inside the device the needle stop material may be adhered, fused or vulcanized to the posterior of the implant or the patch. For this purpose, the needle guard may be dipped silicone that is then heat cured, such that the needle guard is covered by a silicone sheath. This silicone sheath is vulcanized to the silicone patch or posterior of the implant, to prevent movement of the guard inside the implant.

Figure 5:
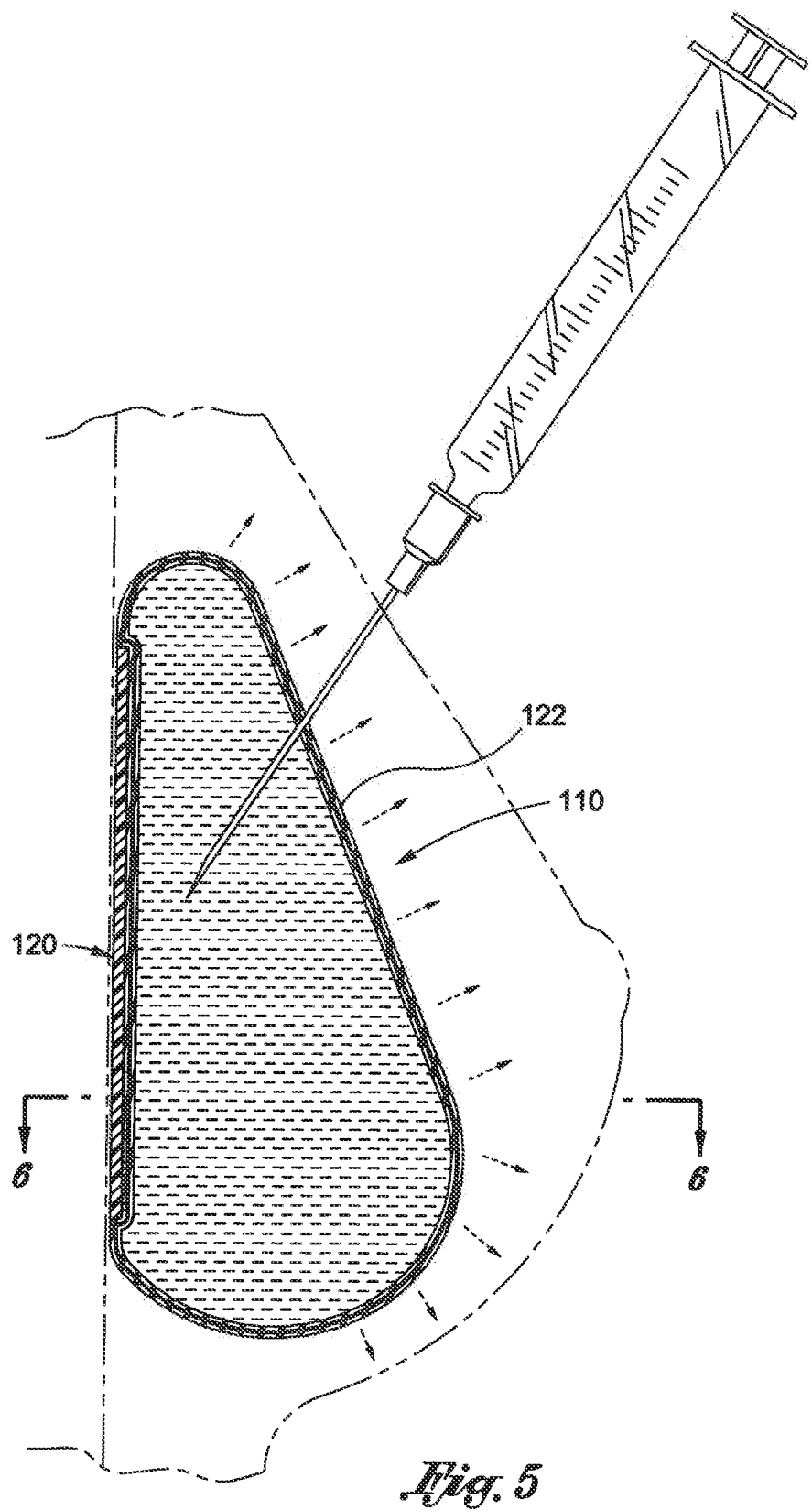
FIG. 5 is a cross-sectional view of another tissue expander in accordance with the invention.
Figure 6:
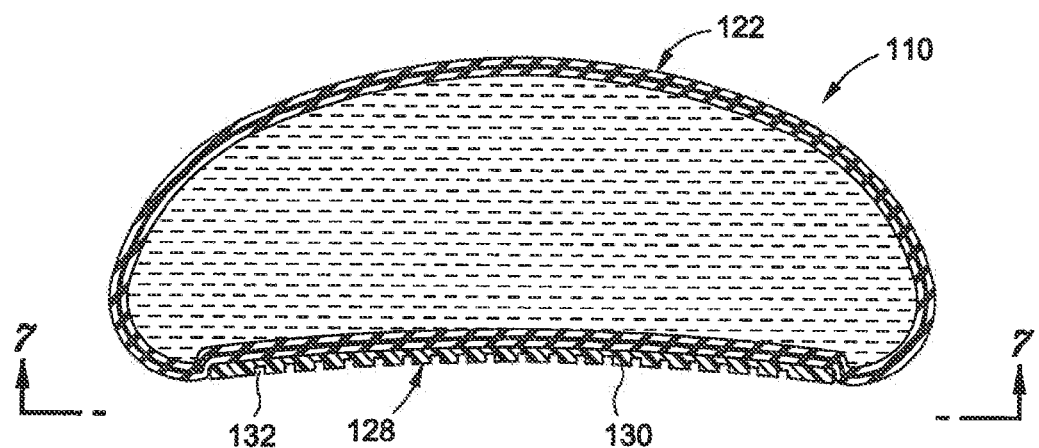
FIG. 6 is a cross-sectional view of yet another tissue expander in accordance with the invention.
Figure 7:
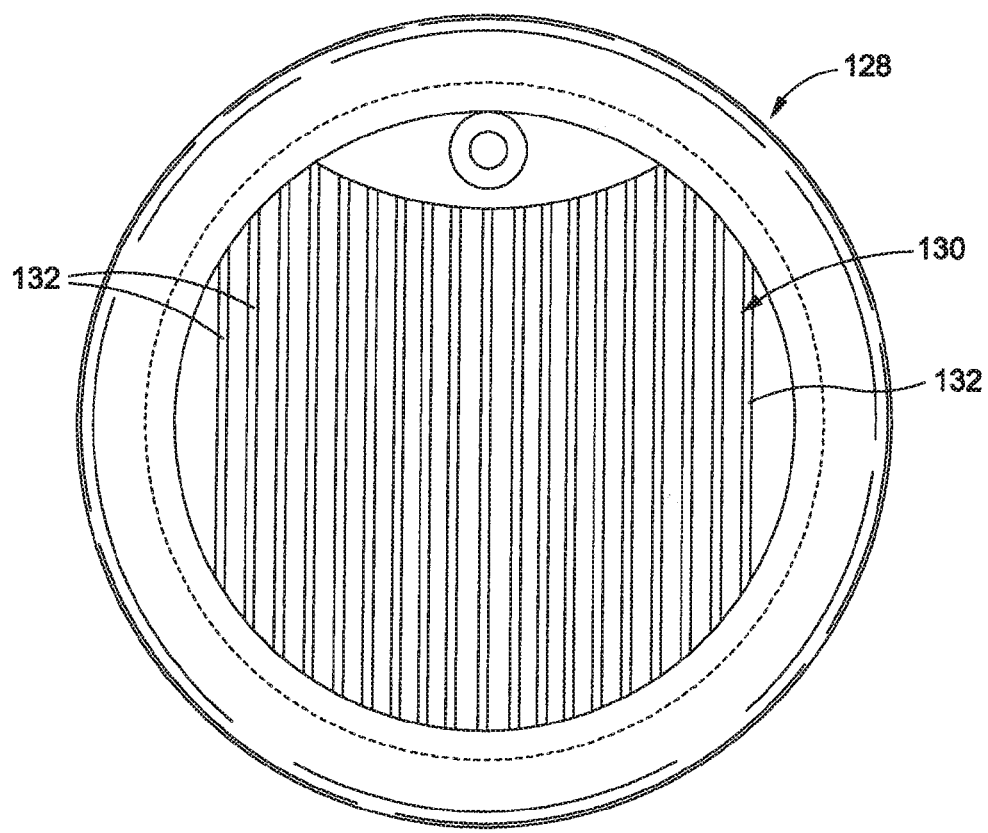
FIG. 7 is a cross-sectional view taken along line 7-7 of FIG. 6.

Another device 110 in accordance with the invention is shown in FIG. 5-7. Device 110 may be substantially identical to device 10 except that device 110 does not include an inner shell 24 or an intermediate layer 26. Device 110 comprises a self-sealing outer layer 122. Self-sealing outer layer 122 may be identical to layer 22 of device 10. Further, rather than needle guard 50, device 110 comprises needle guard 128 which comprises a puncture resistant elastomeric member 130 having grooves 132 for facilitating rolling or folding of device 110 during insertion.

Turning now to FIGS. 11-16a, another device, for example, an inflatable implant, in accordance with the invention is shown generally at 310. Implant 310 may be identical to implant 10 shown in FIG. 3, with the primary difference being that instead of needle guard 50 made up of layers of slats as described elsewhere herein, implant 310 includes a puncture resistant material 314 as shown and now described.

Device 310 includes a inflatable portion 312, and a puncture resistant assembly 314.

Device 310 is expanded or inflated (or deflated) by insertion of a needle 313 (FIG. 1) through inflatable portion 312 (which may be identical to inflatable portion 12 of device 10) and introduction of fluid into a cavity 312a. Instead of inflatable portion 12, it can be appreciated that inflatable portion 312 can include any suitable structure, including an elastomeric bladder having an access port with a needle penetratable septum, or may be made partially or entirely of a puncturable, but self sealing material. Some suitable self sealing materials are described, for example, in U.S. patent application Ser. No. 12/543,795, filed on Aug. 19, 2009, the entire specifications of which are incorporated herein by this reference.

In order to prevent the needle 313 from undesirably penetrating through the device 310, the device is equipped with assembly 314.

Figure 12:
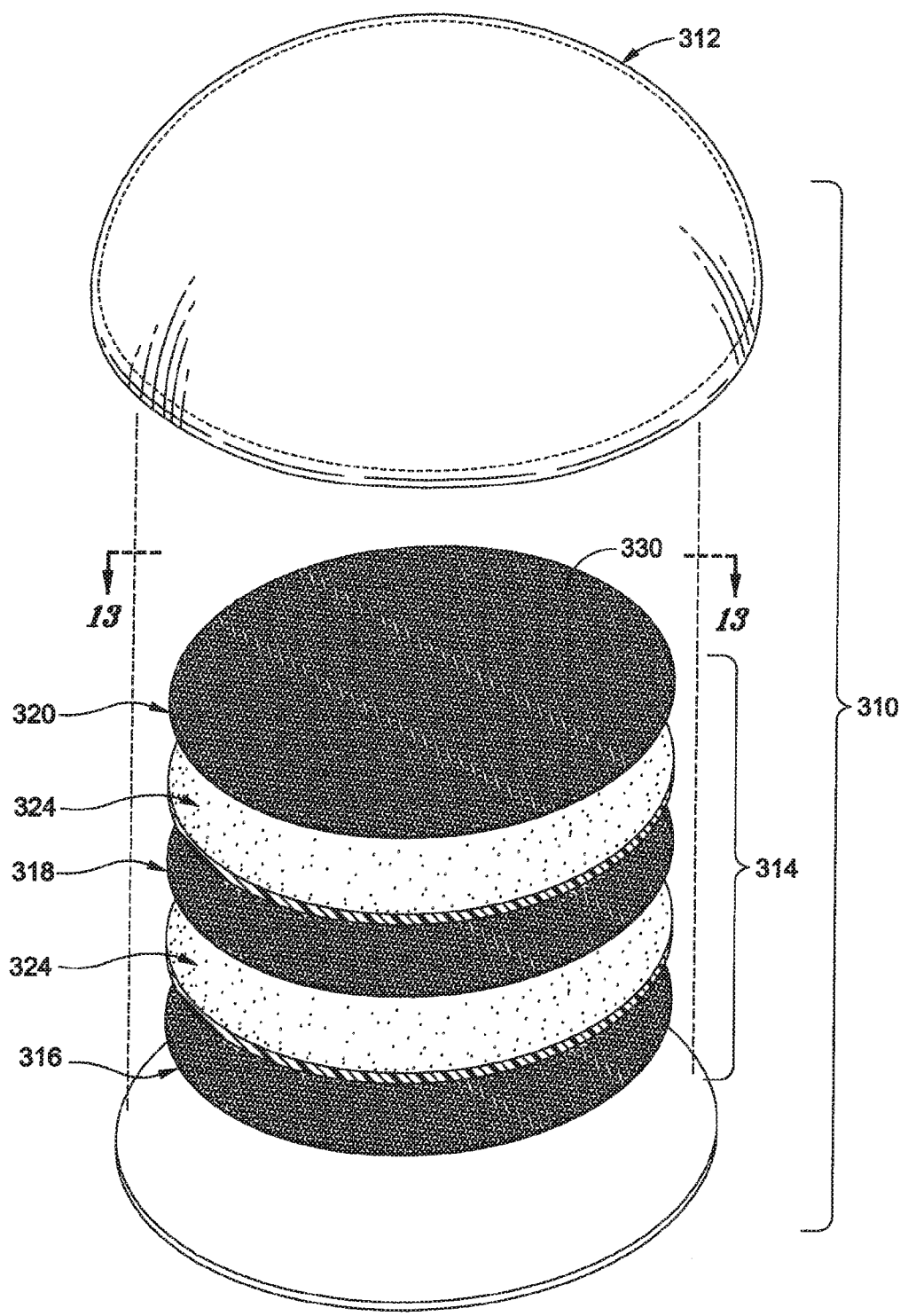
FIG. 12 is an exploded view of the prosthesis shown in FIG. 11 in order to illustrate certain components of the puncture resistant assembly.

Referring now to FIG. 12, the assembly 314 generally comprises a first composite guard 316 and a second composite guard 318. In the shown embodiment, the assembly 314 further includes a third composite guard 320. In other embodiments, only two composite guards or more than three composite guards are provided. An intermediate layer 324 is provided between adjacent guards, for example, between guard 316 and guard 318, and, likewise, between guard 318 and guard 320.

Figure 13:
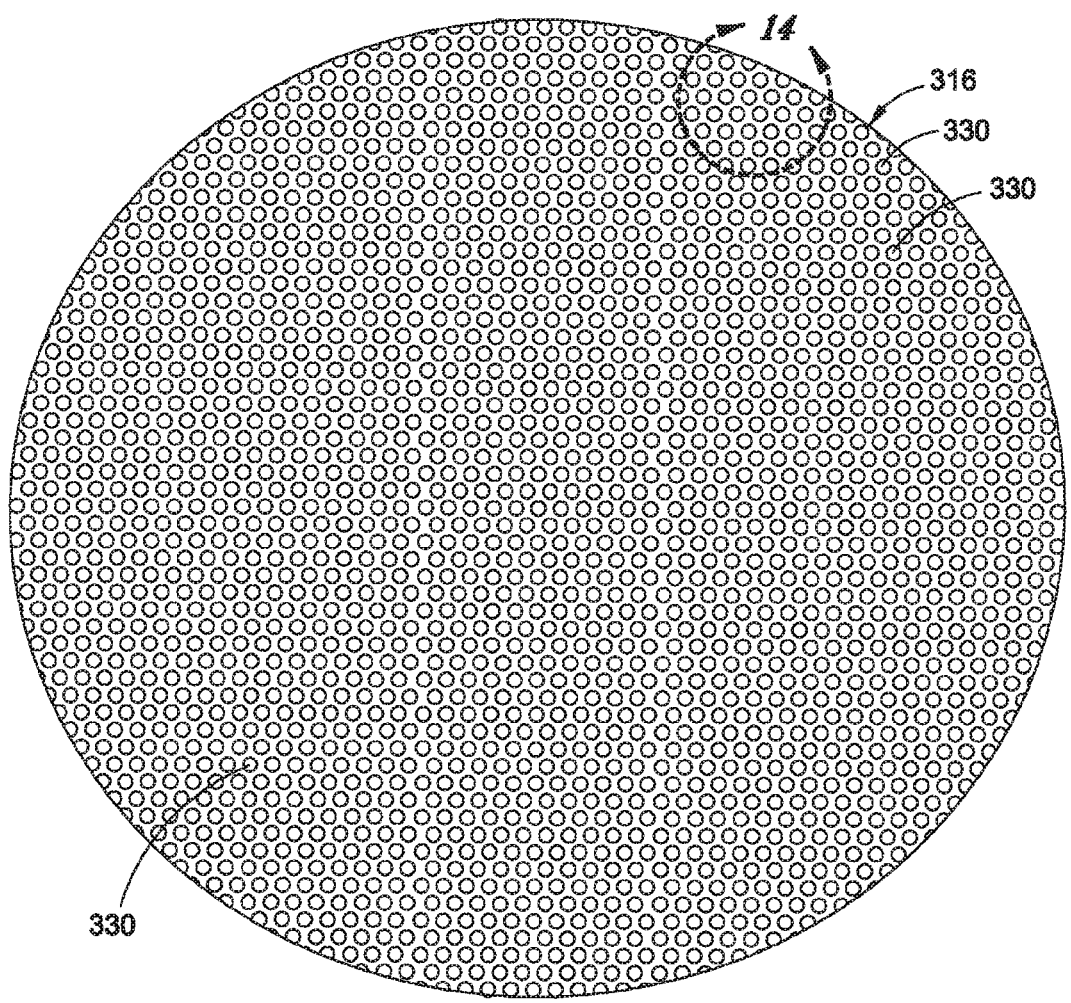
FIG. 13 is a top view of a composite guard which is a component of the puncture resistant assembly shown in FIG. 11.
Figure 14:
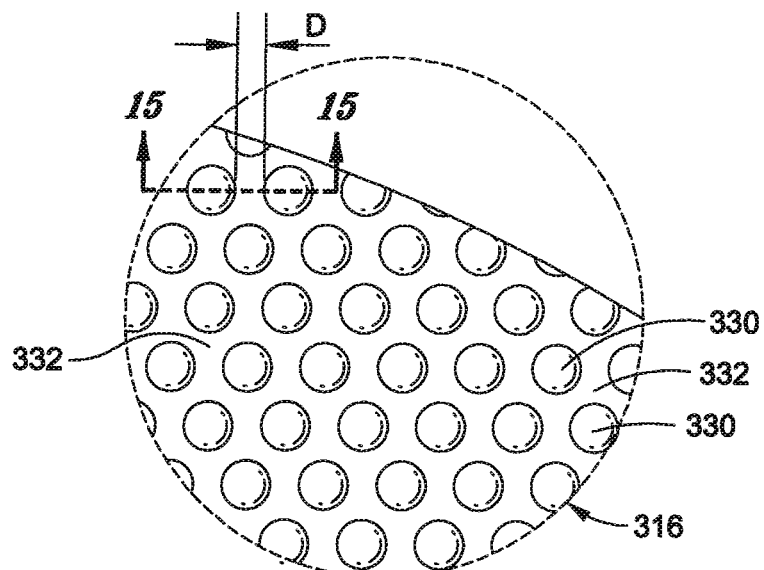
FIG. 14 is a magnified view of a portion of the composite encompassed by line 14 of FIG. 13.

Turning now as well to FIGS. 13 and 14, each of composite guards 316, 318, 320 includes a plurality of, for example, an arrangement, array, or pattern of, puncture resistant members 330, and a flexible substrate 332 having a first side on which the puncture resistant members 330 are disposed in a generally spaced apart fashion.

Figure 11:
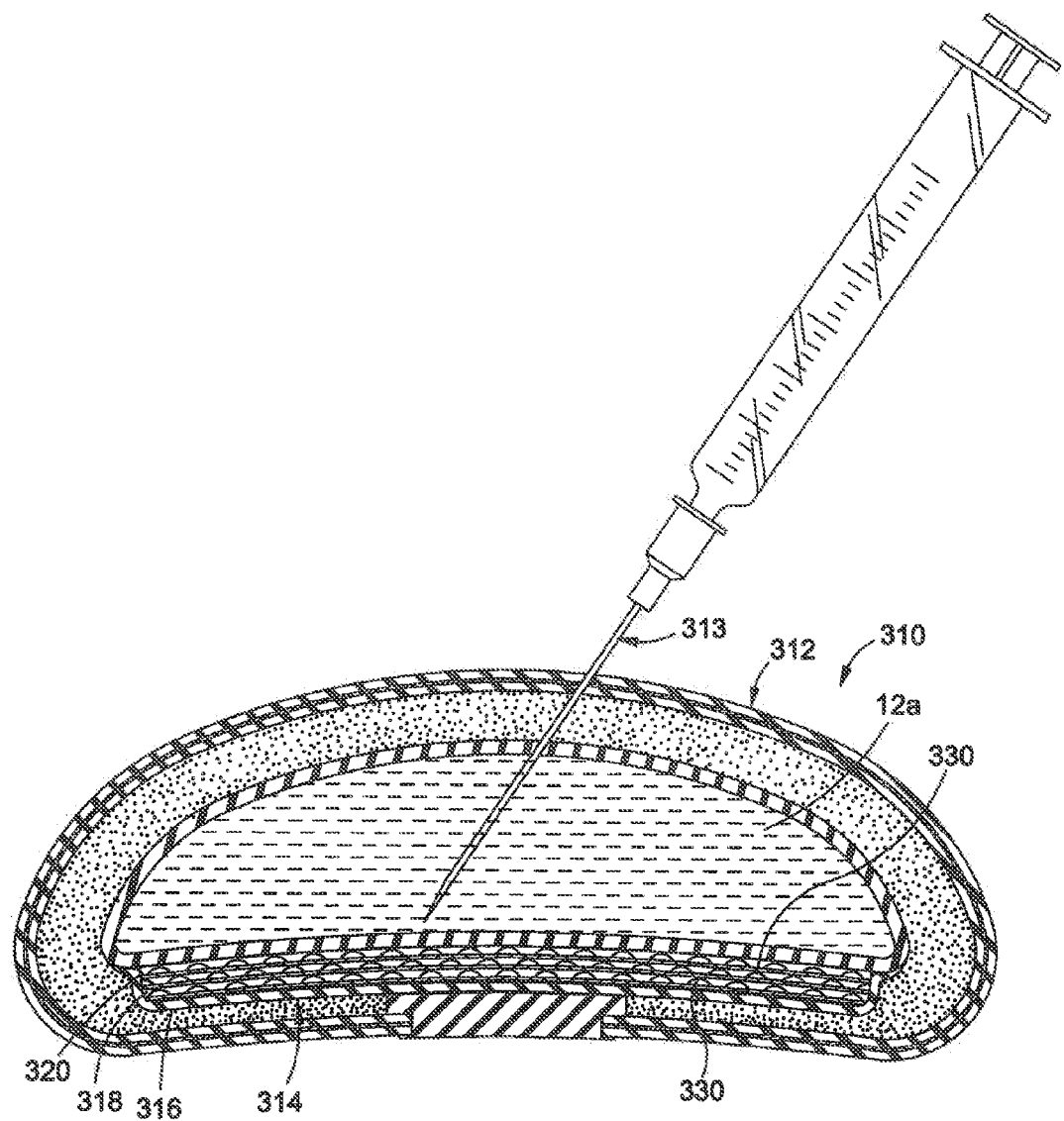
FIG. 11 is cross-sectional view of another inflatable prosthesis of the invention including a puncture resistant assembly.

As can be best appreciated from FIG. 11 (and FIG. 19), the first composite guard 316 and the second composite guard 318 are positioned such that the arrangement of puncture resistant members 330 of the second composite guard 318 are misaligned with the arrangement of puncture resistant members 330 of the first composite guard 316. Similarly, the second composite guard 318 and the third composite guard 320 may be positioned such that the arrangement of puncture resistant members of the third composite guard 320 are misaligned with the arrangement of puncture resistant members of at least one of the first composite guard 316 and the second composite guard 318. Thus, accordingly, the composite guards 316, 318, 320 are arranged relative to one another such that there are no straight line open spaces, or substantial gaps, between members 330 to allow a needle or sharp implement to penetrate entirely through the assembly 314. Yet, advantageously, the assembly 314 as a whole may be quite flexible in that the substrate 332 on which the spaced apart 330 members are disposed is supple, flexible and/or bendable.

Turning specifically to FIG. 12, the intermediate layer 324 may comprise a flexible, connecting material which is effective to couple or bond the first composite guard 316 with the second composite guard 318, and the second composite guard 318 with the third composite guard 320. As shown in FIG. 12, the intermediate layer 324 is positioned between the arrangement of puncture resistant members 330 of the first layer 316 and the flexible substrate 332 of the second layer 318, and another intermediate layer 324 is positioned between the arrangement of puncture resistant members 330 of the second layer 318 and the flexible substrate 332 of the third layer 320.

The composite guards 316, 318, 320 may be identical to one another, and for the sake of simplicity, only the first composite guard 316 will now be described, with the understanding that, in the shown embodiment, what is described for the first composite guard 316 is also applicable to second composite guard 18 and third composite guard 320.

Figure 15:
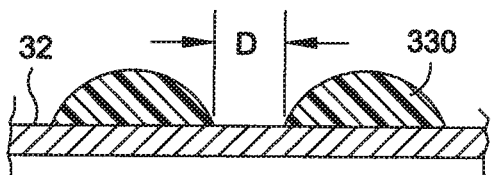
FIG. 15 is a cross-sectional view of the composite guard taken along line 15-15 of FIG. 14.
Figure 16:
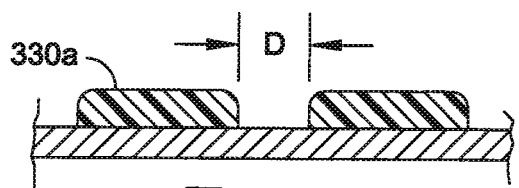
FIG. 16 is a cross-sectional view, similar to the view shown in FIG. 15, of an alternative composite guard in accordance with certain aspects of the invention.
Figure 16A:
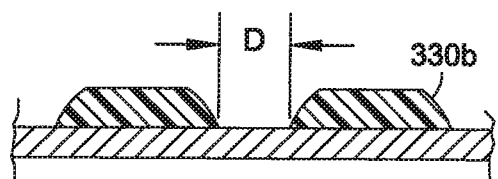
FIG. 16a is a cross-sectional view, similar to the view shown in FIG. 15, of yet another composite guard in accordance with certain aspects of the invention.

The members 330 may be any suitable shape. In FIG. 15, the members 330 are somewhat dome shaped with rounded surfaces. In other embodiments, members 330a may be planar as illustrated in FIG. 16. Alternatively still, the members 330b may include both rounded surface and planar or flat surfaces, such as the members 330b which are dome shaped with a flat upper surface, as illustrated in FIG. 16a.

The members 330 have a thickness of between about 0.1 mm and about 1.0 mm, for example, a thickness of between about 0.2 mm and about 0.5 mm for example, between about 0.1 mm and about 1.0 mm. The members 330 have a spacing D of between about 0.2 mm and about 0.5 mm. The members 30 have a diameter of between about 0.5 mm and about 2.0 mm, for example, a diameter of about 1.5 mm.

In some embodiments, the guard 316 includes between about 50 and about 1000 members per square inch (psi), for example, about 400 psi.

In a specific embodiment, the guard 316 include about 400 members psi, each having a diameter of about 1.5 mm and each being spaced apart about 0.2 mm.

The members 330 (and 330a and 330b) are made of a suitable puncture resistant material, such as an epoxy, polymer, rubber, cermamic or metal, or suitable combination or alloy thereof. For some applications, suitable materials include polyethylene (PE), polypropylene (PP), polyurethane (PU), polyethylene terephthalate (PET), piolycarbonate (PC), polyisoprene (PI), thermoplastic urethanes and thermoplastic polyurethanes (TPU), high durometer silicones, acrylonitrile butadiene styrene (ABS) etc. In some embodiments, the members 330 are made of material selected from acetal, nylon, and polycarbonate. In some embodiments, the members 330 are made of a metal, for example, stainless steel, aluminum, titanium, or other metal.

The flexible substrate 332 may comprise a mesh, film, fabric, elastomer, or other suitable material.

The intermediate layer 324 may be a polymer, for example, an elastomeric polymer, for example, a silicone elastomer, for example, a low durometer silicone rubber.

In some embodiments, the assembly 314 has a resiliency or a shape memory such that it will restore from a folded or rolled configuration to an original, different configuration. The original configuration may be a generally flat or planar configuration. This may be provided by using a suitable intermediate layer material, such as a silicone elastomer that has a shape memory characteristic.

Figure 17:
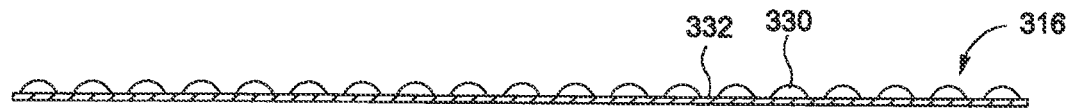
FIGS. 17-19 illustrate steps useful in making some of the puncture resistant assemblies of the present invention.
Figure 18:
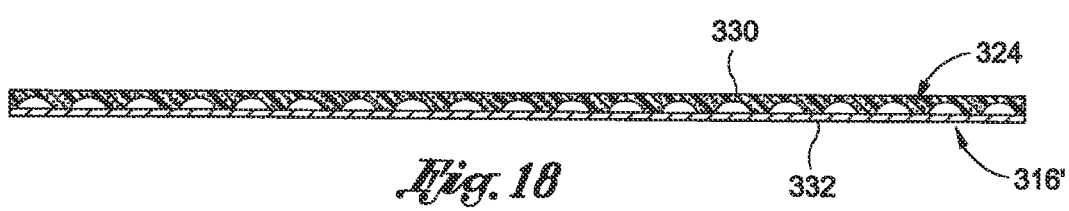
Figure 19:
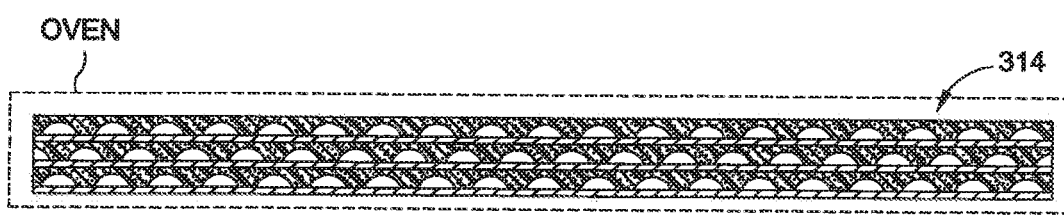

Assembly of the guard assembly 314 may be accomplished as follows and as shown in FIGS. 17-19.

Turning now to FIG. 17, guard 316 generally comprising members 330 and substrate 332, is made by any suitable method, including stencil printing, for example, using equipment and processes used in surface mount technology/PCB fabrication. Other processes that can be used to make the guard 316 include micro-dot dispensing and printing, laser etching. Other suitable methods will be known to those of skill in the art.

Figure 18A:
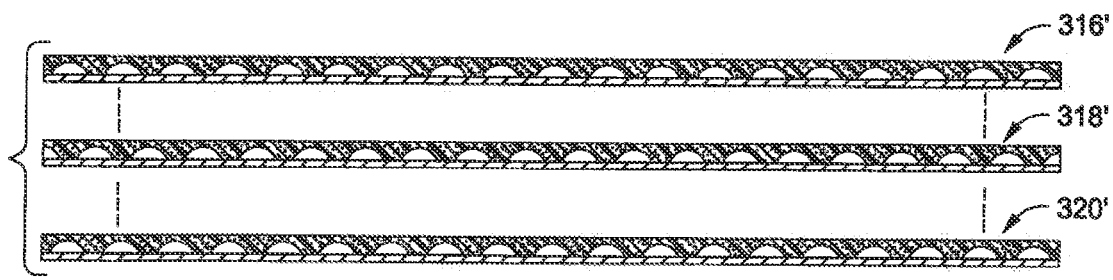

Turning to FIG. 18, intermediate layer 324 may be formed as follows. A suitable material, for example, a sheet of uncured silicone, is placed on one side of the guard 316, for example, on the side having members 30 and substrate 332. The sheet is then subjected to curing conditions to cause the sheet to adhere to the members 330, forming intermediate layer 324 thereon. In the presently described example embodiment, this step is done three times, with three separate guards 316, 318, 320, to form the components 316', 318' and 320' of assembly 314. (See FIG. 18a).

The assembly 314 is then placed in an oven or otherwise subjected to further curing conditions to seal the assembly components together such as shown in FIG. 19.

Figure 20:
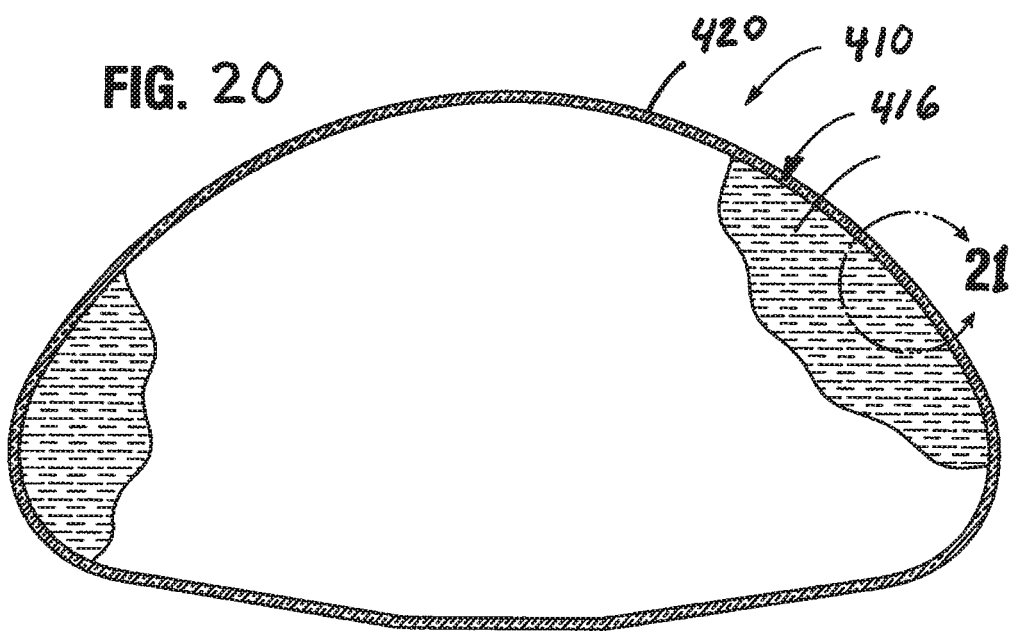
FIG. 20 is a cross sectional representation of a closed self-tissue expander shell comprising a laminate, in accordance with one embodiment of the present invention.

FIG. 20 shows an alternative shell 416 useful for forming a self sealing tissue expander or a more permanent prosthesis 410, in accordance with the invention. Although not shown, it can be appreciated that the tissue expander/prosthesis 410 can include a needle guard 50, 128, 316, forming a posterior surface of prosthesis 410, as described elsewhere herein.

In this embodiment, the shell 416 comprises a laminate 420 made up of layered components, the laminate 420 being formable on a conventional mandrel, using conventional techniques. The shell defines a cavity which is fillable and expandable with a suitable fluid 420.

Figure 21:
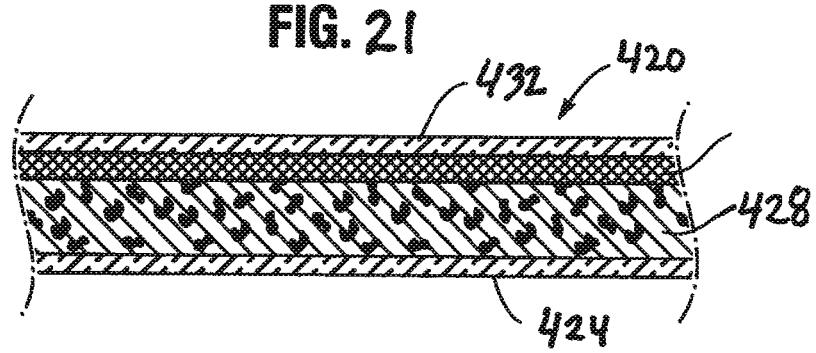
FIG. 21 is an enlarged cross sectional view taken along the line 21 of FIG. 20 more clearly representing the configuration of the laminate of the shell shown in FIG. 20.

With reference to FIG. 21, the laminate 420 includes an elastomer base layer 424, a layer 428 of silicone, which is sufficient thickness for self-sealing of a needle hole therethrough (not shown), and a top layer 432 also formed from an elastomer.

The base and top layer 424, 432 may be formed of any suitable biocompatible elastomer. In a specific embodiment, layers 424 and 432 comprise any suitable silicone elastomer, for example, a silicone elastomer marketed under the name MED 6400, available from Nusil Technology, Carpinteria, Calif. (Shore A 30, ultimate tensile strength 1250 psi, % Elongation 900, tear strength 150 lbf/in.)

Figure 22:
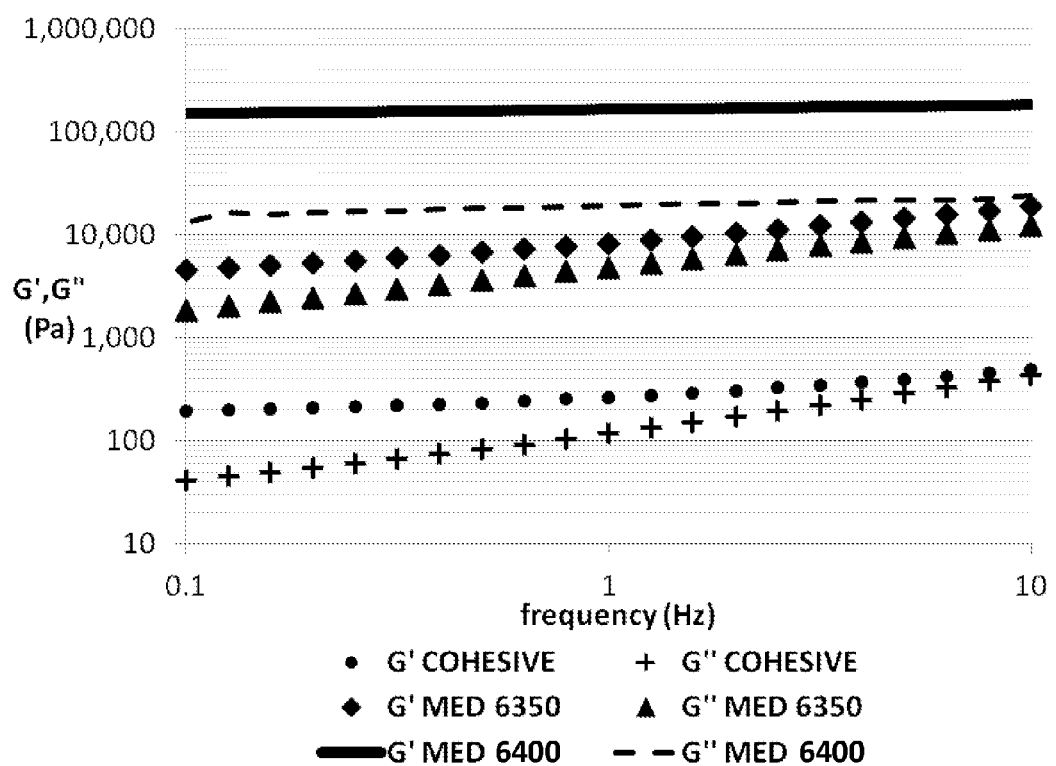
FIG. 22 is a frequency/G',G" chart showing properties of a preferred material for an intermediate layer of laminate of the embodiment shown in FIGS. 20 and 21.

Preferably, the intermediate layer 428 is formed of a soft silicone gel having the viscoelastic properties (dynamic modulus G',G") of a product shown in the chart in FIG. 22, for example, a silicone elastomer marketed under the name MED 6350, also available from NuSil. This preferred material has dynamic modulus G',G" between Nusil MED 6400 and a cohesive silicone gel. In this chart, G' represents storage modulus of material indicative of shape/dimensional stability, and G" is loss modulus of material indicative of flow within material.

The intermediate layer preferably comprises a material with storage modulus at about 0.1, 1 and 10 Hz of about 4490, about 8330 and about 18800 Pa, respectively. Further the material may have a loss modulus at 0.1, 1 and 10 Hz of about 1840, about 4820 and about 12400 Pa, respectively, and a complex viscosity at 0.1, 1 and 10 Hz of about 7720, about 1520 and about 358 Pa·s. For example, the intermediate layer may be Nusil MED 6350.

It has been found that when the base layer 24 has a thickness of about 0.006 inches and a silicone layer 28 has a thickness of between about 0.100 inches and 0.120 inches, and the top layer has a thickness of about 0.006 inches. An internal chamber pressure of about 2.5 psi can be established with expander exterior compressor force of about 40 lbs.

This is important in the effectiveness of the expander to expand tissue, not shown, without undue pressure, as may be the case with prior art tissue expanders. A mesh, for example, a polyester mesh 436 adjacent the intermediate layer, may be utilized for strengthening the laminate with the polyester mesh having a thickness also about 0.006 inches.

As shown in FIG. 1, the tissue expander 10 includes no filling port area with the entire expander 10 having a self-healing characteristics for sealing any hole created by a hypodermic needle when the saline 20 filling process is complete and the needle is removed.

The materials of the present invention also enable mandrel forming of the expander 10.

In that regard, the expander 10 is formed on a mandrel (not shown) having a contoured surface that substantially conforms to a desired shape of the tissue expander 10.

The base layer 24 is coated on the mandrel with a plurality of coats to establish a thickness of about 0.006 inches. The silicone layer 28 is thereafter coated onto the base layer and mandrel and cured with a thickness of about 0.1 inches to 0.12 inches. The mesh 36 may be disposed over the silicone layer 28 and secured thereto by curing of the silicone layer 28.

Thereafter the layer 32 is coated onto the underlying base layer, silicone layer, and mesh to a thickness of about 0.006 inches.

The layers 24, 28, 32 may be cured in a conventional manner.

As hereinabove noted, the total thickness of the base layer 24, silicone layer 28, and top layer 32 enable an internal chamber pressure of about 2.5 psi with an expander exterior compressor force of about 40 lbs.

While this invention has been described with respect to various specific examples and embodiments, it is to be understood that the invention is not limited thereto and that it can be variously practiced within the scope of the invention.

What is claimed is:

1. A flexible self-sealing prosthesis comprising:
a shell made of a flexible laminate defining a fillable chamber;
the laminate comprising a base layer formed from an elastomer, a top layer formed from an elastomer, and an intermediate layer disposed between the base layer and the top layer, the intermediate layer being a silicone elastomer of sufficient thickness for self-sealing of a needle hole therethrough;
a total thickness of the laminate enabling an internal chamber pressure of 2.5 psi with an exterior compressive force of 40 pounds;
wherein the intermediate layer comprises a material with a storage modulus at 0.1, 1 and 10 Hz of 4490, 8330 and 18800 Pa, respectively.

2. The prosthesis according to claim 1 wherein the intermediate layer material has a loss modulus at 0.1, 1 and 10 Hz of 1840, 4820 and 12400 Pa, respectively.

3. The prosthesis according to claim 2 wherein the intermediate layer material has a complex viscosity at 0.1, 1 and 10 Hz of 7720, 1520 and 358 Pa·s, respectively.

4. The prosthesis according to claim 1 wherein the base layer has a thickness of 0.006 inches, the intermediate layer has a thickness of between 0.100 inches and 0.120 inches, and the top layer has a thickness of 0.006 inches.

5. The prosthesis according to claim 1 further comprising a polyester mesh layer adjacent the intermediate layer.

6. The prosthesis of claim 1 further comprising a puncture resistant guard coupled to the shell.

7. A flexible self-sealing prosthesis comprising:
a shell made of a flexible laminate defining a fillable chamber;
the laminate comprising a base layer formed from an elastomer, a top layer formed from an elastomer, and an intermediate layer disposed between the base layer and the top layer, the intermediate layer being a silicone elastomer of sufficient thickness for self-sealing of a needle hole therethrough;

a total thickness of the laminate enabling an internal chamber pressure of 2.5 psi with an exterior compressive force of 40 pounds;

wherein the intermediate layer has a thickness between 0.100 inches and 0.120 inches and comprises a material with a storage modulus at 0.1, 1 and 10 Hz of 4490, 8330 and 18800 Pa, respectively, a loss modulus at 0.1, 1 and 10 Hz of 1840, 4820 and 12400 Pa, respectively, and a complex viscosity at 0.1, 1 and 10 Hz of 7720, 1520 and 358 Pa·s, respectively.

* * * * *

UNITED STATES PATENT AND TRADEMARK OFFICE
CERTIFICATE OF CORRECTION

PATENT NO. : 8,636,797 B2  
APPLICATION NO. : 13/105715  
DATED : January 28, 2014  
INVENTOR(S) : Kaustubh S. Chitre et al.

Page 1 of 1

It is certified that error appears in the above-identified patent and that said Letters Patent is hereby corrected as shown below:

In the Specification

In column 8, line 30, delete "polyethylene" and insert -- poly(ethylene --, therefor.

In column 8, line 55, before "curved" delete "a".

In column 14, line 33, delete "(and 330a" and insert -- (330a --, therefor.

In column 14, line 35, delete "cermamic" and insert -- ceramic --, therefor.

In column 14, line 38, delete "piolycarbonate" and insert -- polycarbonate --, therefor.

Signed and Sealed this  
Twelfth Day of May, 2015

Michelle K. Lee  
*Director of the United States Patent and Trademark Office*